US012799131B2

(12) United States Patent
Yang et al.

(10) Patent No.: US 12,799,131 B2
(45) Date of Patent: Nov. 17, 2026

(54) SESQUITERPENE DERIVATIVE AND PHARMACEUTICAL COMPOSITION THEREOF, AND THEIR PREPARATION METHODS AND USE

(71) Applicant: TIANJIN JIKUN MEDICAL TECHNOLOGY CO., LTD., Tianjin (CN)

(72) Inventors: Cheng Yang, The Woodlands, TX (US); Guang Yang, Tianjin (CN); Honggang Zhou, Tianjin (CN)

(73) Assignee: TIANJIN JIKUN MEDICAL TECHNOLOGY CO., LTD. (CN)

( * ) Notice: Subject to any disclaimer, the term of this patent is extended or adjusted under 35 U.S.C. 154(b) by 418 days.

(21) Appl. No.: 18/575,976

(22) PCT Filed: May 10, 2023

(86) PCT No.: PCT/CN2023/093156

§ 371 (c)(1),
(2) Date: Jan. 2, 2024

(87) PCT Pub. No.: WO2023/221828

PCT Pub. Date: Nov. 23, 2023

(65) Prior Publication Data

US 2024/0317772 A1 Sep. 26, 2024

(30) Foreign Application Priority Data

May 16, 2022 (CN) ......................... 202210527640.2

(51) Int. Cl.
*C07D 493/10* (2006.01)
*A61K 31/365* (2006.01)
*A61K 39/395* (2006.01)
*A61P 35/00* (2006.01)

(52) U.S. Cl.
CPC .......... *C07D 493/10* (2013.01); *A61K 31/365* (2013.01); *A61K 39/3955* (2013.01); *A61P 35/00* (2018.01)

(58) Field of Classification Search
None
See application file for complete search history.

(56) References Cited

FOREIGN PATENT DOCUMENTS

| | | |
|---|---|---|
| CN | 106474109 A | 3/2017 |
| CN | 106474110 A | 3/2017 |
| CN | 106478569 A | 3/2017 |
| CN | 106496243 A | 3/2017 |
| CN | 108003174 A | 5/2018 |
| CN | 112724109 A | 4/2021 |
| CN | 114773356 A | 7/2022 |

OTHER PUBLICATIONS

Machine Translation of CN 106478569 A, Translated by Patent Translate Espacenet.org on Apr. 20, 2026, 58 pages. (Year: 2017).*
D'Alessio et al. "PD-1 Blockade for Hepatocellular Carcinoma: Current Research and Future Prospects" Journal of Hepatocellular Carcinoma, 2021, 8, 887-897. DOI: 10.2147/JHCS284440 (Year: 2021).*
Office Action for Application Serial No. CN202210527640.2 dated Aug. 25, 2022.
International Search Report for Application No. PCT/CN2023/093156 dated Aug. 12, 2023.

* cited by examiner

*Primary Examiner* — Jennifer A Berrios
*Assistant Examiner* — Sophia Reilly
(74) *Attorney, Agent, or Firm* — C. Tumey Law Group PLLC

(57) ABSTRACT

Provided are a sesquiterpene derivative represented by formula (I) or a pharmaceutically acceptable salt thereof, a pharmaceutical composition including the same and a PD-1 antibody as active components, as well as a preparation method and use thereof; in formula (I), $R_1$ and $R_2$ independently are selected from the group consisting of alkyl and hydroxyalkyl, with the proviso that $R_1$ and $R_2$ are not simultaneously methyl.

Formula (I)

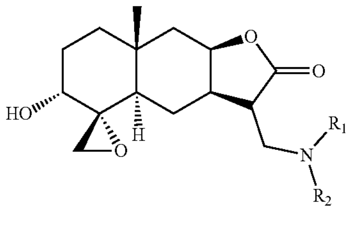

18 Claims, No Drawings

SESQUITERPENE DERIVATIVE AND PHARMACEUTICAL COMPOSITION THEREOF, AND THEIR PREPARATION METHODS AND USE

CROSS REFERENCE TO RELATED APPLICATION

The application is a national stage application of International Patent Application No. PCT/CN2023/093156, filed on May 10, 2023, which claims the priority and benefit of Chinese Patent Application No. 2022105276402, entitled "Sesquiterpene derivative and pharmaceutical composition thereof, and their preparation methods and use" filed with the China National Intellectual Property Administration (CNIPA) on May 16, 2022. The two applications each are incorporated herein by reference in its entirety as part of this application.

TECHNICAL FIELD

The present disclosure relates to the field of medicinal chemistry, and in particular to a sesquiterpene derivative and a pharmaceutical composition thereof, and their preparation methods and use.

BACKGROUND

The occurrence and development of tumors depend on a variety of mechanisms, among which immune escape (namely avoiding being recognized and eliminated by the immune system) is an extremely important mechanism. The body's immune system can monitor "non-self" mutant cells and specifically eliminate these cells through a cellular immune mechanism, thereby maintaining a stability of the body's internal environment. However, under the influence of various factors, tumors escape from the body's immune surveillance and undergo immune escape, and a malignant biological behavior of the tumors may be further accelerated, thereby promoting tumor proliferation, invasion, and metastasis.

Programmed death-1 (PD-1) is an important immunosuppressive transmembrane protein expressed on the surface of T cells. In a tumor microenvironment, T cells are induced to overexpress PD-1 molecules, while tumor cells express their ligands PD-L1 or PD-L2. When the ligand PD-L1 or PD-L2 is linked to PD-1, T cells are unable to detect tumors and then send signals to the immune system to attack the tumors. Therefore, a PD-1 monoclonal antibody immunotherapy that blocks PD-1/PD-L1 signaling pathways and recovers an immune killing function of T cells has also emerged. According to statistics, there are 154 companies that research and develop the PD-1 antibody in the world, many of which are well-known companies such as Merck, BMS, Junshi, Innovent, and Hengrui. Currently, there are 6 PD-1 antibodies approved for marketing in China, targeting more than ten indications including non-small cell lung cancer (NSCLC), gastric cancer, breast cancer, and renal cell cancer.

However, PD-1 antibodies have certain limitations in clinical application, most notably a poor response rate to tumor patients. According to clinical statistics, the PD-1 antibody has the best response rate to melanoma patients at about 40%, followed by NSCLC patients at about 25% to 30%, liver cancer patients at about 20%, and patients with most other tumors at generally less than 15%. In particular, this antibody is essentially unresponsive to patients with pancreatic cancer (at a response rate of less than 1%). The reasons for the poor response rate of PD-1 antibodies to tumor patients are relatively complex, and the mechanism is unclear and still under study.

At present, there are already some combination schemes that can appropriately improve the anti-tumor effect of PD-1 antibodies. For example, chemotherapy drug paclitaxel, platinum-based chemotherapy drugs, and radiotherapy combined with PD-1 antibodies to treat tumors can significantly improve the response of the patient's tumor lesions to the PD-1, thus improving therapeutic effects. In addition, a therapy by using targeted drugs such as EGFR and VEGFR combined with the PD-1 antibodies has also achieved desirable therapeutic effects, benefiting patients significantly.

Despite this, means for combination therapy are still highly limited and still less effective against originally low-response tumor types. Accordingly, it is of great clinical significance to screen and develop compounds that can enhance immunotherapy.

Information disclosed in the background section is provided merely for enhancing the comprehension of the general background of the present disclosure, and shall not be regarded as acknowledgement or any form of suggestion that the information constitutes the prior art commonly known to those of ordinary skill in the art.

SUMMARY

Objects

The present disclosure is to provide a sesquiterpene derivative or a pharmaceutically acceptable salt thereof, a preparation method thereof, a pharmaceutical composition including the same and a PD-1 antibody, and use thereof in preparation of a drug for treating a tumor. In the present disclosure, the sesquiterpene derivative or the pharmaceutically acceptable salt thereof could significantly enhance a response and a therapeutic effect of the PD-1 antibody on tumors. The combination administration of the derivative or the salt with the PD-1 antibody exhibits a significant synergistic effect and shows an extremely strong anti-tumor activity.

Solutions

To achieve the above objects, the present disclosure provides the following technical solutions.

In a first aspect, the present disclosure provides a sesquiterpene derivative or a pharmaceutically acceptable salt thereof, the sesquiterpene derivative having a structure represented by formula (I):

(I)

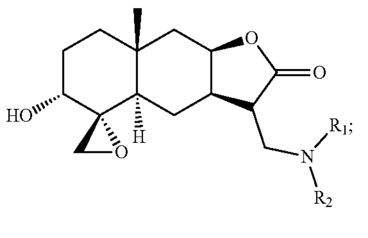

where $R_1$ and $R_2$ independently are selected from the group consisting of alkyl and hydroxyalkyl, with the proviso that $R_1$ and $R_2$ are not simultaneously methyl.

In some embodiments, the alkyl is $C_1$ to $C_4$ alkyl. In further embodiments, the alkyl is $C_1$ to $C_3$ alkyl.

In some embodiments, the hydroxyalkyl is $C_1$ to $C_4$ hydroxyalkyl. In further embodiments, the hydroxyalkyl is $C_1$ to $C_3$ hydroxyalkyl.

In some embodiments, the sesquiterpene derivative is a compound selected from the group consisting of:

1

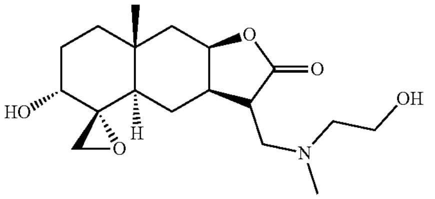

2

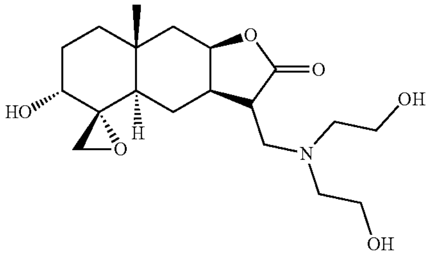

and

3

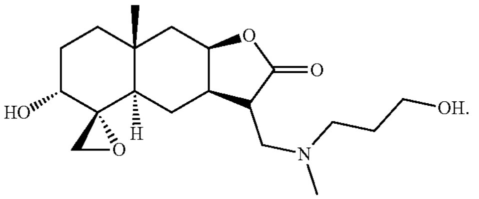

In some embodiments, the pharmaceutically acceptable salt of the sesquiterpene derivative is a salt prepared from the sesquiterpene derivative and an inorganic acid or an organic acid.

In some embodiments, the inorganic acid is selected from the group consisting of hydrofluoric acid, hydrochloric acid, hydrobromic acid, hydroiodic acid, sulfuric acid, nitric acid, phosphoric acid, and carbonic acid.

In some embodiments, the organic acid is selected from the group consisting of citric acid, maleic acid, D-malic acid, L-malic acid, DL-malic acid, D-lactic acid, L-lactic acid, DL-lactic acid, oxalic acid, methanesulfonic acid, p-toluenesulfonic acid, tartaric acid, malonic acid, succinic acid, fumaric acid, benzoic acid, and substituted benzoic acid.

In some embodiments, the pharmaceutically acceptable salt of the sesquiterpene derivative is a fumarate of the sesquiterpene derivative.

In some embodiments, the pharmaceutically acceptable salt of the sesquiterpene derivative is a compound selected from the group consisting of:

4

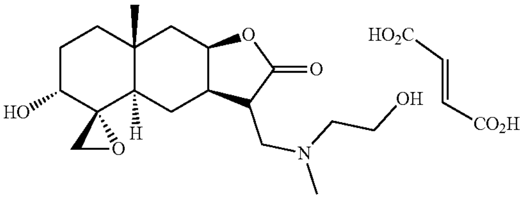

-continued

5

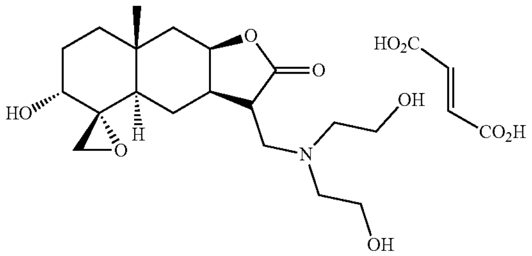

and

6

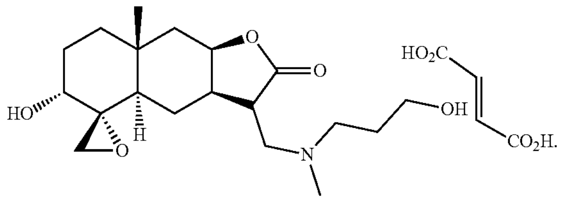

In a second aspect, the present disclosure provides a method for preparing the sesquiterpene derivative or the pharmaceutically acceptable salt thereof as described in the first aspect by a synthetic route as follows:

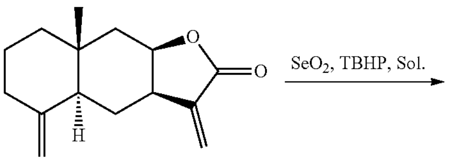

Isoalantolactone

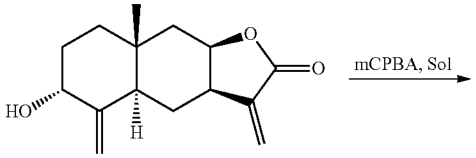

Intermediate 1

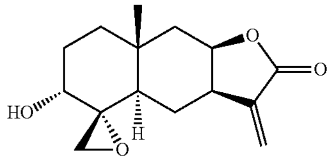

CP0105

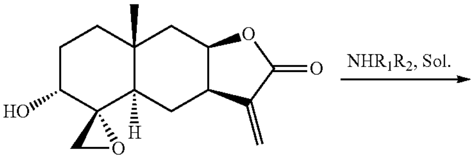

CP0105

-continued

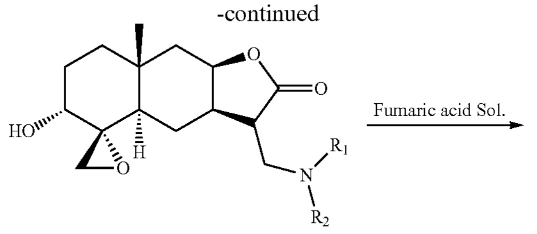

1-3

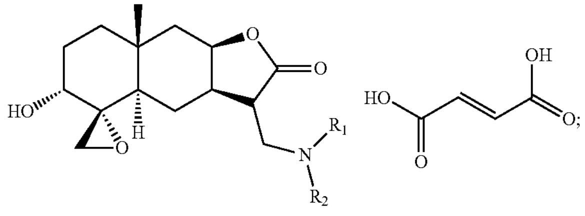

4-6 wherein the Sol. represents a solvent, and the solvent is one or more selected from the group consisting of dichloromethane (DCM), chloroform, tetrahydrofuran (THF), methanol, ethanol, toluene, acetonitrile, ethyl acetate, N,N'-dimethylformamide (DMF), dimethyl sulfoxide (DMSO), and water.

In a third aspect, the present disclosure provides a pharmaceutical composition, including the sesquiterpene derivative or the pharmaceutically acceptable salt thereof as described in the first aspect, a PD-1 antibody (preferably a PD-1 monoclonal antibody), and a pharmaceutically acceptable carrier and/or excipient.

In the pharmaceutical composition according to the present disclosure, the sesquiterpene derivative or the pharmaceutically acceptable salt thereof serves as a first active ingredient, and the PD-1 antibody serves as a second active ingredient. In some embodiments, the sesquiterpene derivative or the pharmaceutically acceptable salt thereof and the PD-1 antibody are in a same preparation unit, or in different preparation units.

In some embodiments, a mass ratio of the sesquiterpene derivative or the pharmaceutically acceptable salt thereof to the PD-1 antibody is in a range of (1-20):1, preferably 10:1.

In a fourth aspect, the present disclosure provides use of the sesquiterpene derivative or the pharmaceutically acceptable salt thereof as described in the first aspect or the pharmaceutical composition as described in the third aspect in preparation of a drug for treating a tumor.

In some embodiments, the tumor is selected from the group consisting of melanoma, lung cancer, pancreatic cancer, liver cancer, colorectal cancer, gastric cancer, and glioma.

Beneficial Effects

The sesquiterpene derivative or the pharmaceutically acceptable salt thereof according to the present disclosure could significantly enhance the response and the therapeutic effect of the PD-1 antibody on tumors. The combination administration of the derivative or the salt with the PD-1 antibody exhibits a significant synergistic effect and shows an extremely strong anti-tumor activity. The present disclosure provides a new concept for clinical treatment of tumors, which has potential clinical application values and broad clinical application prospects.

DETAILED DESCRIPTION OF THE EMBODIMENTS

In order to make the objects, technical solutions, and advantages of the embodiments of the present disclosure clearer, the technical solutions of the embodiments of the present disclosure are described clearly and completely below. Apparently, the described examples are some rather than all of the embodiments of the present disclosure. Based on the embodiments of the present disclosure, all other embodiments obtained by those of ordinary skill in the art without creative efforts should fall within the scope of the present disclosure.

In addition, to better illustrate the present disclosure, numerous specific details are given in the following specific examples. Persons skilled in the art should understand that the present disclosure could also be implemented without certain specific details. In some embodiments, materials, components, methods, and means that are well-known to those skilled in the art are not described in detail in order to highlight the concept of the present disclosure.

Unless otherwise expressly stated, the terms such as "include", "comprise", "contain" and variations thereof throughout the specification and claims are understood as including the elements or components described, without excluding other elements or other components.

Unless otherwise specified, the experimental methods used in the following examples may be performed by conventional methods.

Unless otherwise specified, the materials or reagents used in the following examples may be commercially available.

Example 1: Preparation of Compound 1

Compound 1 has a structure of:

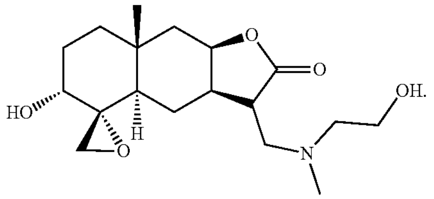

A preparation process was performed as follows:

Selenium dioxide (2.86 g, 25.8 mmol) was dissolved in DCM (250 mL) at 0 °C, tert-butyl hydroperoxide (15.5 mL) was added thereto, and a resulting mixture was then stirred for 30 min to obtain a first system. A solution of isoalantolactone (30 g, 0.129 mol) in DCM (250 mL) was slowly added into the first system, and a resulting mixture system was subjected to a first reaction by stirring at room temperature for 8 h. After that, the first reaction was quenched by using a saturated sodium thiosulfate aqueous solution (500 mL). A liquid separation was conducted, then a resulting first aqueous phase was extracted with DCM (300 mL×3), and a resulting first organic phases were combined, dried, concentrated, and then recrystallized with a mixed solvent of petroleum ether/ethyl acetate, obtaining intermediate 1 (19.5 g of a white solid with a yield of 61%), which was used directly in the next step.

Intermediate 1 (19.5 g, 78.5 mmol) was dissolved in DCM (100 mL) at 0 °C to obtain a second system. A solution of m-chloroperoxybenzoic acid (16.3 g, 94.2 mmol) in DCM (300 mL) was slowly added dropwise into the second system, and a resulting mixed system was subjected to a second reaction at room temperature for 2 h. After that, the second reaction was quenched with saturated sodium thiosulfate (300 mL). A resulting second aqueous phase was extracted with ethyl acetate (3×200 mL), and a resulting second organic phase was washed once with a saturated solution of $NaHCO_3$ (100 mL), then dried with anhydrous $Na_2SO_4$, and filtered to remove solid. A resulting mother liquor was concentrated, obtaining a crude product of compound CP0105. The crude product of compound CP0105 was recrystallized with ethyl acetate/petroleum ether, obtaining compound CP0105 (16.8 g, with a yield of 81%).

Compound CP0105 (1.00 g, 3.78 mmol) was dissolved in THF (16 mL) to obtain a third system. N-methylaminoethanol (1.42 g, 18.9 mmol) was added to the third system, and the third system was subjected to a third reaction by stirring at 25 °C for 4 h. After the third reaction was completed, the THF was removed by concentration under reduced pressure to obtain a crude product of Compound 1. The crude product was purified by a silica gel flash column chromatography (DCM:methanol=20:1), obtaining Compound 1 (1.13 g of a white solid, with a yield of 88%).

Compound 1 was detected and its NMR data were as follows:

$^1H$ NMR (400 MHZ, DMSO) δ4.76 (d, J=4.3 Hz, 1H), 3.90 (t, J=5.2 Hz, 1H), 3.75 (t, J=6.3 Hz, 2H), 3.46 (d, J=2.9 Hz, 1H), 3.38 (dt, J=10.4, 5.4 Hz, 1H), 3.22 (t, J=5.2 Hz, 1H), 3.02 (d, J=4.5 Hz, 1H), 2.89-2.72 (m, 7H), 2.67 (dt, J=12.7, 6.4 Hz, 2H), 2.36 (dd, J=13.0, 2.3 Hz, 1H), 2.30-2.15 (m, 1H), 2.07-1.93 (m, 1H), 1.92-1.69 (m, 3H), 1.60 (ddd, J=13.7, 5.9, 2.5 Hz, 1H), 1.52-1.39 (m, 1H), 1.11 (s, 3H), 0.91 (q, J=12.9 Hz, 1H). $^{13}C$ NMR (100 MHz, DMSO) δ177.5, 77.5, 71.1, 60.8, 59.3, 58.6, 56.4, 52.5, 50.4, 48.0, 44.4, 42.2, 38.4, 36.8, 34.2, 27.7, 17.9, 15.5. HRMS(ESI): m/z calcd for $C_{18}H_{29}NO_5Na^+$ [M+Na]$^+$ 362.1938, found 362.1933.

Example 2: Preparation of a Fumarate of Compound 1 (i.e., Compound 4)

Compound 4 has the following structure:

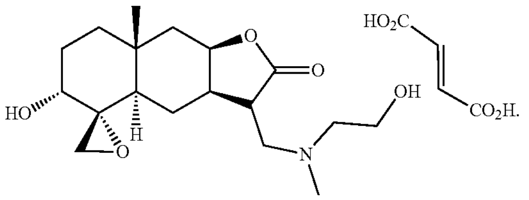

Compound 1 (1.08 g, 3.19 mmol) prepared in Example 1 was dissolved in THF (20 mL) and stirred to be uniform to obtain a fourth system, and fumaric acid (352 mg, 3.03 mmol) was then added thereto. A resulting reaction system was subjected to a fourth reaction by stirring at room temperature for 3 h. After the fourth reaction was completed, THF was removed by concentration under reduced pressure, and then ethyl acetate (100 mL) was added into a system obtained after removing THF to obtain a suspension; the suspension was subjected to suction filtration to obtain Compound 4 (1.26 g of a white solid, with a yield of 83%).

Compound 4 was detected and its NMR data were as follows:

$^1H$ NMR (400 MHZ, DMSO) δ6.80 (s, 2H), 4.76 (d, J=4.3 Hz, 1H), 3.90 (t, J=5.2 Hz, 1H), 3.75 (t, J=6.3 Hz, 2H), 3.46 (d, J=2.9 Hz, 1H), 3.38 (dt, J=10.4, 5.4 Hz, 1H), 3.22 (t, J=5.2 Hz, 1H), 3.02 (d, J=4.5 Hz, 1H), 2.89-2.72 (m, 7H), 2.67 (dt, J=12.7, 6.4 Hz, 2H), 2.36 (dd, J=13.0, 2.3 Hz, 1H), 2.30-2.15 (m, 1H), 2.07-1.93 (m, 1H), 1.92-1.69 (m, 3H), 1.60 (ddd, J=13.7, 5.9, 2.5 Hz, 1H), 1.52-1.39 (m, 1H), 1.11 (s, 3H), 0.91 (q, J=12.9 Hz, 1H). $^{13}C$ NMR (100 MHz, DMSO) δ177.5, 167.4, 134.8, 77.5, 71.1, 60.8, 59.3, 58.6, 56.4, 52.5, 50.4, 48.0, 44.4, 42.2, 38.4, 36.8, 34.2, 27.7, 17.9, 15.5. HRMS(ESI): m/z calcd for $C_{18}H_{29}NO_5Na^+$[M+Na]$^+$ 362.1938, found 362.1933.

Example 3: Preparation of Compound 2

Compound 2 has the following structure:

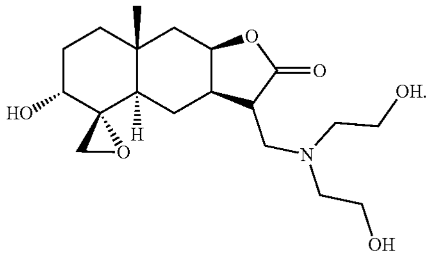

A preparation process was performed as follows:

The preparation process was performed according to the preparation process of Compound 1 in Example 1 except that ethylene glycol amine (1.99 g, 18.9 mmol) was used, obtaining compound 2 (879 mg of a white solid, with a yield of 63%).

Compound 2 was detected and its NMR data were as follows:

$^1H$ NMR (400 MHZ, DMSO) δ 4.48 (s, 1H), 3.47 (q, J=5.3, 4.8 Hz, 3H), 3.18 (s, 1H), 3.13-3.04 (m, 1H), 2.86-2.53 (m, 9H), 2.49-2.34 (m, 4H), 2.08 (d, J=12.7 Hz, 1H), 1.95 (d, J=15.3 Hz, 1H), 1.82-1.67 (m, 1H), 1.64-1.45 (m, 3H), 1.34 (dd, J=14.0, 5.2 Hz, 1H), 1.20 (d, J=12.5 Hz, 1H), 0.83 (s, 3H), 0.63 (q, J=12.7 Hz, 1H). $^{13}C$ NMR (100 MHz, DMSO) δ 177.6, 77.4, 71.1, 60.8, 58.8, 58.6, 56.3, 50.0, 48.0, 41.3, 38.4, 36.8, 34.7, 34.2, 27.7, 17.9, 15.5. HRMS (ESI):m/z calcd for $C_{19}H_{31}NO_6Na^+$[M+Na]$^+$ 392.2044, found 392.2039.

Example 4: Preparation of a Fumarate of Compound 2 (i.e., Compound 5)

Compound 5 has the following structure:

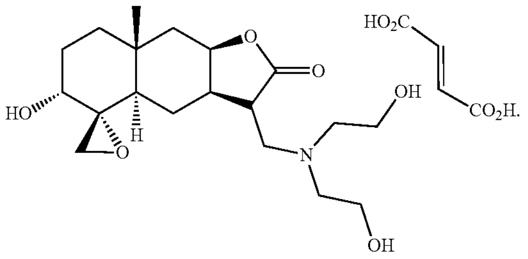

The preparation process was performed according to according to the preparation process of Compound 4 in Example 2, except that Compound 2 (878 mg, 2.38 mmol) prepared in Example 3 and fumaric acid (262 mg, 2.26 mmol) were used, obtaining Compound 5 (674 mg of a white solid, with a yield of 58%).

Compound 5 was detected and its NMR data were as follows:

$^1$H NMR (400 MHZ, DMSO) δ6.61 (d, J=3.2 Hz, 2H), 4.48 (s, 1H), 3.47 (q, J=5.3, 4.8 Hz, 3H), 3.18 (s, 1H), 3.13-3.04 (m, 1H), 2.86-2.53 (m, 9H), 2.49-2.34 (m, 4H), 2.08 (d, J=12.7 Hz, 1H), 1.95 (d, J=15.3 Hz, 1H), 1.82-1.67 (m, 1H), 1.64-1.45 (m, 3H), 1.34 (dd, J=14.0, 5.2 Hz, 1H), 1.20 (d, J=12.5 Hz, 1H), 0.83 (s, 3H), 0.63 (q, J=12.7 Hz, 1H). $^{13}$C NMR (100 MHz, DMSO) δ177.6, 166.2, 134.1, 77.4, 71.1, 60.8, 58.8, 58.6, 56.3, 50.0, 48.0, 41.3, 38.4, 36.8, 34.7, 34.2, 27.7, 17.9, 15.5. HRMS(ESI):m/z calcd for $C_{19}H_{31}NO_6Na^+[M+Na]^+$ 392.2044, found 392.2039.

Example 5: Preparation of Compound 3

Compound 3 has the following structure:

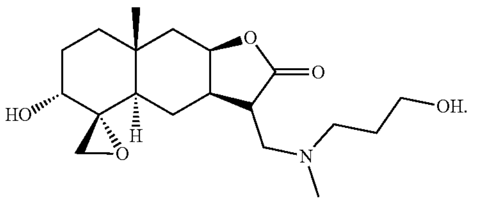

A preparation process was performed as follows:

The preparation process was performed according to the preparation process of Compound 1 in Example 1, except that N-methylaminopropanol (1.65 g, 18.9 mmol) was used, obtaining Compound 3 (1.32 g of a white solid, with a yield of 99%).

Compound 3 was detected and its NMR data were as follows:

$^1$H NMR (400 MHz, DMSO) δ5.11-4.48 (m, 1H), 3.67 (q, J=6.2, 5.3 Hz, 2H), 3.50-3.31 (m, 3H), 3.21-2.96 (m, 2H), 2.96-2.69 (m, 7H), 2.67 (q, J=6.1, 5.6 Hz, 2H), 2.39-2.28 (m, 1H), 2.26-2.14 (m, 1H), 2.07-1.69 (m, 6H), 1.62-1.51 (m, 1H), 1.44 (qt, J=10.6, 7.2, 6.4 Hz, 1H), 1.07 (s, 3H), 0.88 (q, J=12.8 Hz, 1H). $^{13}$C NMR (100 MHz, DMSO) δ 177.3, 77.6, 71.1, 60.9, 59.1, 54.1, 52.0, 48.1, 44.1, 41.5, 41.3, 38.5, 36.8, 34.7, 34.3, 29.2, 27.7, 18.0, 15.6. HRMS(ESI):m/z calcd for $C_{19}H_{31}NO_5Na^+[M+Na]^+$ 376.2094, found 376.2093.

Example 6: Preparation of a Fumarate of Compound 3 (i.e., Compound 6)

Compound 6 has the following structure:

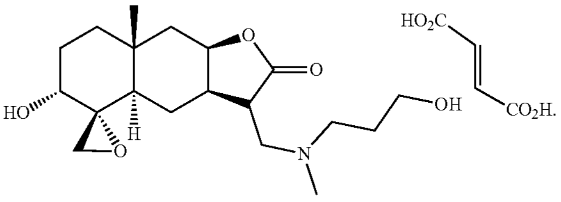

The preparation process was performed according to the preparation process of Compound 4 in Example 2 except that Compound 3 (1.32 g, 3.74 mmol) prepared in Example 5 and fumaric acid (412 mg, 3.56 mmol) were used, obtaining Compound 6 (1.42 g of a white solid, with a yield of 81%).

Compound 6 was detected and its NMR data were as follows:

$^1$H NMR (400 MHZ, DMSO) δ6.82 (s, 2H), 5.11-4.48 (m, 1H), 3.67 (q, J=6.2, 5.3 Hz, 2H), 3.50-3.31 (m, 3H), 3.21-2.96 (m, 2H), 2.96-2.69 (m, 7H), 2.67 (q, J=6.1, 5.6 Hz, 2H), 2.39-2.28 (m, 1H), 2.26-2.14 (m, 1H), 2.07-1.69 (m, 6H), 1.62-1.51 (m, 1H), 1.44 (qt, J=10.6, 7.2, 6.4 Hz, 1H), 1.07 (s, 3H), 0.88 (q, J=12.8 Hz, 1H). $^{13}$C NMR (100 MHz, DMSO) δ177.3, 166.6, 134.4, 77.6, 71.1, 60.9, 59.1, 54.1, 52.0, 48.1, 44.1, 41.5, 41.3, 38.5, 36.8, 34.7, 34.3, 29.2, 27.7, 18.0, 15.6. HRMS(ESI): m/z calcd for $C_{19}H_{31}NO_5Na^+[M+Na]^+$ 376.2094, found 376.2093.

Comparative Example: Preparation of Compound 7 as a Control

Compound 7 has the following structure:

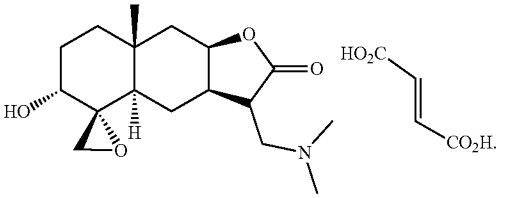

A preparation process was performed as follows:

Compound CP0105 (1.00 g, 3.78 mmol, which was prepared according to the relevant method in Example 1) was dissolved in THF (16 mL), and dimethylamine (2 M in THF, 9.46 mL, 18.9 mmol) was added thereto to obtain a reaction system. The reaction system was subjected to a first reaction by stirring for 4 h at 25 °C. After the first reaction was completed, the solvent THF was removed by rotary evaporation, and a resulting product was concentrated and then dissolved again in THF (20 mL) and stirred to be uniform. Fumaric acid (346 mg, 2.98 mmol) was added thereto, and a second reaction was conducted by stirring at room temperature for 3 h. After the second reaction was completed, the THF was removed by concentration under reduced pressure, and then ethyl acetate (100 mL) was added into a resulting system after removing the THF to obtain a suspension. The suspension was subjected to suction filtration to obtain Compound 7 (951 mg of a white solid, with a yield of 52%).

Compound 7 was detected and its NMR data were as follows:

$^1$H NMR (400 MHZ, $CDCl_3$) δ6.58 (s, 2H), 4.50 (q, J=2.8, 2.0 Hz, 1H), 3.24-3.05 (m, 2H), 2.75 (d, J=4.5 Hz, 1H), 2.62 (dd, J=12.8, 10.4 Hz, 1H), 2.50-2.45 (m, 3H), 2.44-2.37 (m, 1H), 2.26 (s, 6H), 2.08 (dd, J=13.0, 2.4 Hz, 1H), 1.96 (dd, J=15.4, 2.0 Hz, 1H), 1.74 (tt, J=15.3, 3.6 Hz, 1H), 1.63-1.46 (m, 3H), 1.30 (ddd, J=13.6, 5.8, 2.4 Hz, 1H), 1.25-1.14 (m, 1H), 0.83 (s, 3H), 0.64 (q, J=12.9 Hz, 1H). $^{13}$C NMR (100 MHz, $CDCl_3$) δ177.6, 167.0, 134.8, 78.0, 71.5, 61.3, 54.1, 48.5, 45.1, 44.7, 41.7, 38.9, 37.2, 35.2, 34.7, 28.2, 18.4, 16.0. HRMS(ESI):m/z calcd for $C_{17}H_{27}NO_4Na^+[M+Na]^+$ 332.1832, found 332.1838.

Example 7: An Anti-Tumor Effect of a Combination Therapy of Compounds According to the Present Disclosure and a PD-1 Monoclonal Antibody Tumor cells B16F10, LLC, PAN02, H22, CT26, MFC, and GL261 (purchased from Biological Industries) in good growth status were collected, separately washed twice with 1×PBS, and a total number of the cells was counted with a cell counter, and a cell solution was separately diluted with 1×PBS to obtain a cell suspension of $1\times10^7$ cells/mL.

The mice used in this experiment were purchased from Beijing Vital River Laboratory (Beijing, China). The above different types of tumor cells were inoculated into different types of mice to produce corresponding tumor-bearing mice, and the correspondences are as follows.

Tumor cell B16F10 corresponds to female mice C57BL/6 aged 6-8 weeks; Tumor cell LLC corresponds to female mice Balb/c aged 6-8 weeks; Tumor cell PAN02 corresponds to female mice C57BL/6J aged 6-8 weeks; Tumor cell H22 corresponds to female mice C57BL/6 aged 6-8 weeks; Tumor cell CT26 corresponds to female mice Balb/c aged 6-8 weeks; Tumor cell MFC corresponds to female mice BALB/c-nu/nu aged 6-8 weeks; and Tumor cell GL261 corresponds to female mice C57BL/6 aged 6-8 weeks.

The above cell suspensions were separately inoculated into the axilla of forelimb of the mice at an inoculation volume of $1\times10^6$ tumor cells per mouse (i.e., 100 μL cell suspension per mouse); when an average tumor-volume exceeded 100 $cm^3$ (a difference in tumor-volume between individuals did not exceed 10%), the mice were randomly divided into the following types of groups (8 mice in each group):

groups of small-molecular drugs:

Compounds 4, 5, 6, and 7 (the compound 7 was used as a control compound) were orally administered to mice in respective group every day at a dose of 150 mg/kg, separately;

a group of PD-1 monoclonal antibody:

the PD-1 monoclonal antibody was injected intraperitoneally into mice every three days, at 10 mg/kg each time; and groups of combined administration:

each of the above small-molecular drugs and the PD-1 monoclonal antibody were jointly administered to the mice, separately, according to the above respective administration method and dosage.

After the experiment was completed, the mice were euthanized, tumor tissues thereof were collected, and volume and weight of the tumor tissues were tested to calculate a tumor inhibition rate.

Tumor inhibition rate=(1−tumor weight of treatment group/tumor weight of control group)×100%

The experimental results are shown in Table 1.

Table 1 Inhibition rates of each test group on a series of tumors

| Administration | Tumor inhibition rate/% | | | | | | |
|---|---|---|---|---|---|---|---|
| group | B16F10 | LLC | PAN02 | H22 | CT26 | MFC | GL261 |
| PD-1 monoclonal antibody | 18 | 11 | 0 | 41 | 8 | 12 | 1 |
| Compound 4 | 23 | 24 | 22 | 26 | 31 | 27 | 23 |
| Compound 5 | 24 | 26 | 19 | 31 | 52 | 44 | 19 |
| Compound 6 | 31 | 29 | 31 | 39 | 41 | 52 | 29 |
| Control compound 7 | 41 | 44 | 43 | 52 | 60 | 38 | 39 |
| Compound 4 + PD-1 | 87 | 90 | 88 | 83 | 84 | 85 | 80 |
| Compound 5 + PD-1 | 87 | 69 | 75 | 86 | 84 | 85 | 80 |
| Compound 6 + PD-1 | 87 | 90 | 89 | 88 | 87 | 91 | 89 |
| Compound 7 + PD-1 | 67 | 52 | 66 | 49 | 65 | 45 | 46 |

-continued

As shown in Table 1, the combined administration of compound 4, 5, or 6 with the PD-1 monoclonal antibody makes mouse tumor cells B16F10, LLC, PAN02, H22, CT26, MFC, and GL261 that are originally unresponsive or low-responsive to the PD-1 monoclonal antibody significantly respond to immunotherapy with the PD-1 monoclonal antibody. In particular, PAN02 cells that are completely unresponsive to the PD-1 monoclonal antibody or GL261 cells that has extremely low response to the PD-1 monoclonal antibody both produce a tumor inhibition rate of up to 89% (combined administration with compound 6). Even for other tumor cells, the tumor inhibition rate is increased by about 9 times compared with the PD-1 monoclonal antibody group alone. Moreover, compared with the compound alone group, the tumor inhibition rate of combined administration group of the compound 4, 5, or 6 with the PD-1 monoclonal antibody could be increased by up to 4 times. In addition, the tumor inhibition rate of the combined administration group of the compound 4, 5, or 6 with the PD-1 monoclonal antibody is also much higher than that of the combined administration group of the control compound 7 and the PD-1 monoclonal antibody. These results all show that the combined administration of the compound in the present disclosure with the PD-1 monoclonal antibody could significantly enhance the response of tumor cells to the PD-1 monoclonal antibody, and a tumor inhibitory effect is also significantly higher than that of the compound alone. That is, the combination therapy exhibits a significant synergistic effect, and thereby showing an extremely strong anti-tumor activity.

Finally, it should be noted that the foregoing embodiments are only used to illustrate the technical solutions of the present disclosure, and are not intended to limit the present disclosure. Although the present disclosure is described in detail with reference to the foregoing embodiments, a person of ordinary skill in the art should understand that he/she could still modify the technical solutions described in the foregoing embodiments, or make equivalent substitutions to some technical features therein. These modifications or substitutions do not make the essence of the corresponding technical solutions depart from the spirit and scope of technical solutions of the present disclosure.

What is claimed is:

1. A sesquiterpene derivative or a pharmaceutically acceptable salt thereof, the sesquiterpene derivative having a structure represented by formula (I):

(I)

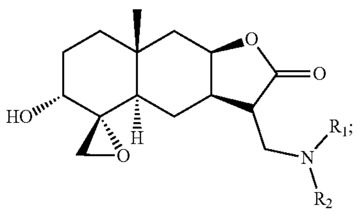

wherein R1 is selected from the group consisting of $C_1$ to $C_4$ alkyl and $C_1$ to $C_4$ hydroxyalkyl, and R2 is $C_1$ to $C_4$ hydroxyalkyl.

2. The sesquiterpene derivative or the pharmaceutically acceptable salt thereof as claimed in claim 1, wherein the $R_1$ is selected from the group consisting of $C_1$ to $C_3$ alkyl and $C_1$ to $C_3$ hydroxyalkyl.

3. The sesquiterpene derivative or the pharmaceutically acceptable salt thereof as claimed in claim 1, wherein the $R_2$ is $C_1$ to $C_3$ hydroxyalkyl.

4. The sesquiterpene derivative or the pharmaceutically acceptable salt thereof as claimed in claim 1, wherein the sesquiterpene derivative is a compound selected from the group consisting of:

1

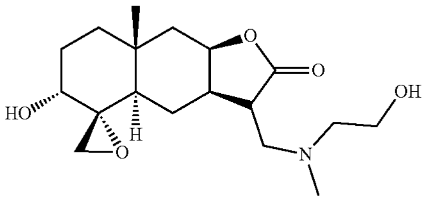

2

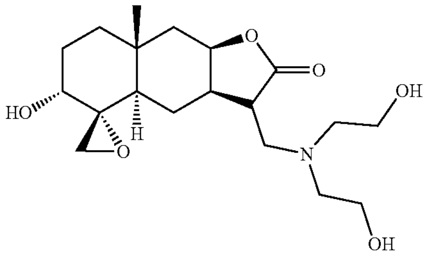

and

3

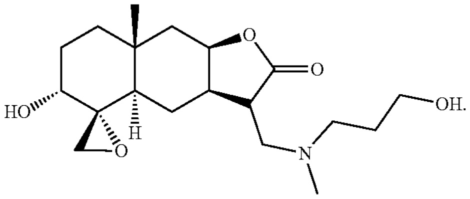

5. The sesquiterpene derivative or the pharmaceutically acceptable salt thereof as claimed in claim 1, wherein the pharmaceutically acceptable salt of the sesquiterpene derivative is a salt prepared from the sesquiterpene derivative and an inorganic acid or an organic acid;

the inorganic acid is selected from the group consisting of hydrofluoric acid, hydrochloric acid, hydrobromic acid, hydroiodic acid, sulfuric acid, nitric acid, phosphoric acid, and carbonic acid; and the organic acid is selected from the group consisting of citric acid, maleic acid, D-malic acid, L-malic acid, DL-malic acid, D-lactic acid, L-lactic acid, DL-lactic acid, oxalic acid, methanesulfonic acid, p-toluenesulfonic acid, tartaric acid, malonic acid, succinic acid, fumaric acid, benzoic acid, and substituted benzoic acid.

6. The sesquiterpene derivative or the pharmaceutically acceptable salt thereof as claimed in claim 5, wherein the pharmaceutically acceptable salt of the sesquiterpene derivative is a fumarate of the sesquiterpene derivative.

7. The sesquiterpene derivative or the pharmaceutically acceptable salt thereof as claimed in claim 6, wherein the pharmaceutically acceptable salt of the sesquiterpene derivative is a compound selected from the group consisting of:

4

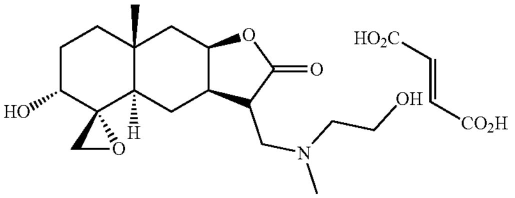

5

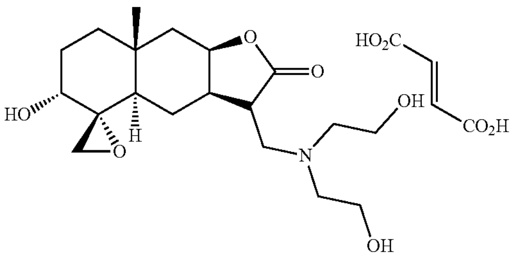

and

6

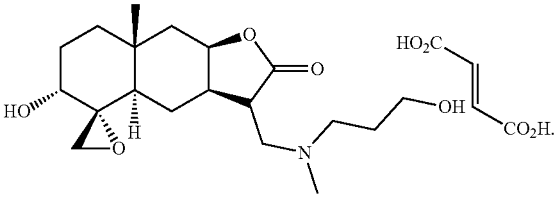

8. A method for preparing the sesquiterpene derivative or the pharmaceutically acceptable salt thereof as claimed in claim 1, comprising synthesizing the sesquiterpene derivative by a first route as follows:

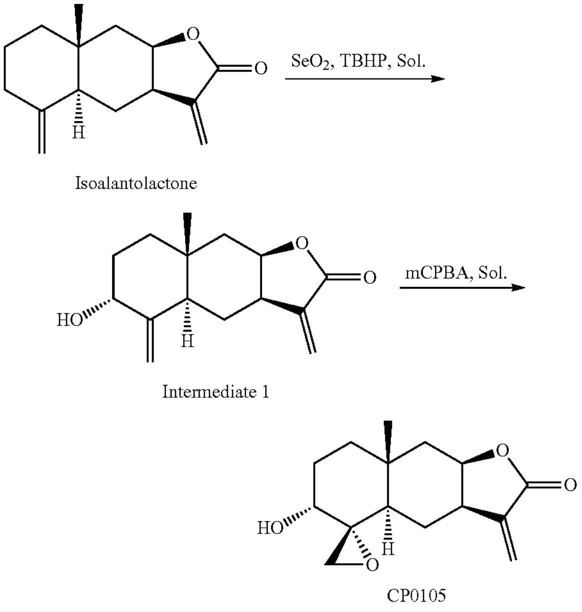

-continued

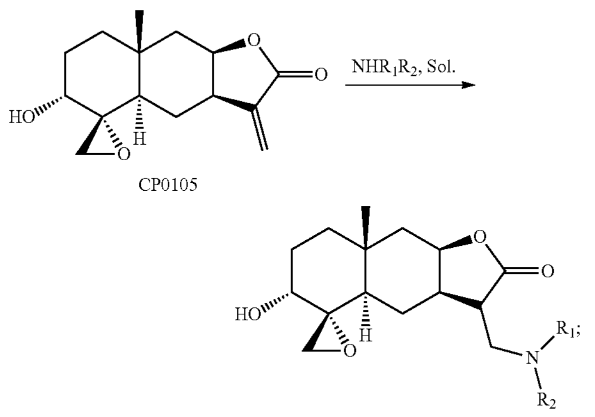

CP0105

1-3 wherein the Sol represents a solvent.

9. The method as claimed in claim 8, comprising synthesizing the fumarate of the sesquiterpene derivative by a second route as follows:

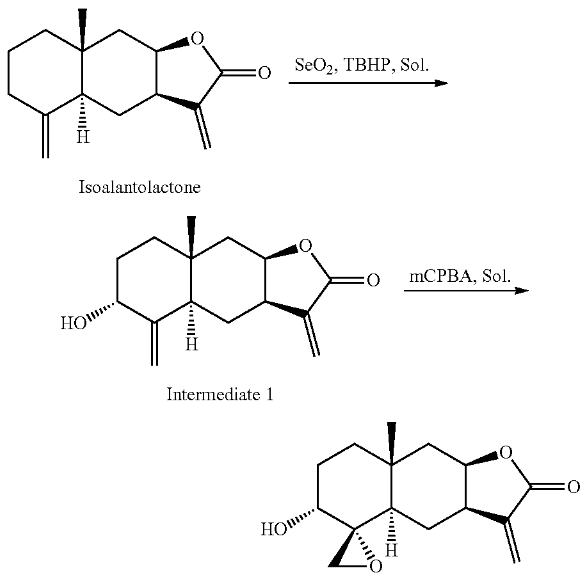

Isoalantolactone

Intermediate 1

CP0105

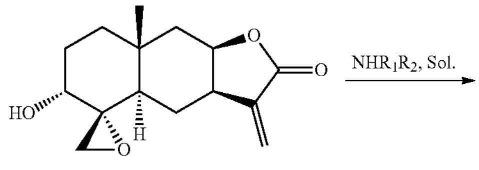

CP0105

-continued

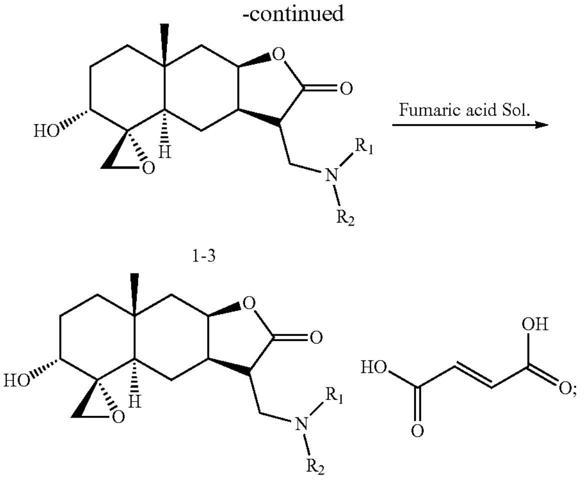

1-3

4-6 wherein the Sol represents the solvent.

10. The method as claimed in claim 8, wherein the Sol is one or more selected from the group consisting of dichloromethane (DCM), chloroform, tetrahydrofuran (THF), methanol, ethanol, toluene, acetonitrile, ethyl acetate, N,N'-dimethylformamide (DMF), dimethyl sulfoxide (DMSO), and water.

11. A pharmaceutical composition, comprising the sesquiterpene derivative or the pharmaceutically acceptable salt thereof as claimed in any-one-of-claim 1, a programmed death-1 (PD-1) antibody, and a pharmaceutically acceptable carrier and/or excipient.

12. The pharmaceutical composition as claimed in claim 11, wherein the PD-1 antibody is a PD-1 monoclonal antibody.

13. The pharmaceutical composition as claimed in claim 11, wherein a mass ratio of the sesquiterpene derivative or the pharmaceutically acceptable salt thereof to the PD-1 antibody is in a range of 1-20:1.

14. The pharmaceutical composition as claimed in claim 13, wherein the mass ratio of the sesquiterpene derivative or the pharmaceutically acceptable salt thereof to the PD-1 antibody is 10:1.

15. The pharmaceutical composition as claimed in claim 13, wherein the sesquiterpene derivative or the pharmaceutically acceptable salt thereof and the PD-1 antibody are in a same preparation unit, or in different preparation units.

16. A method for treating a tumor, comprising administering the sesquiterpene derivative or the pharmaceutically acceptable salt thereof as claimed in claim 1 to a subject in need thereof.

17. The method as claimed in claim 16, wherein the tumor is selected from the group consisting of melanoma, lung cancer, pancreatic cancer, liver cancer, colorectal cancer, gastric cancer, and glioma.

18. A method for treating a tumor, comprising administering the pharmaceutical composition as claimed in claim 11 to a subject in need thereof.

* * * * *